(12) United States Patent
Virr et al.

(10) Patent No.: US 11,642,553 B2
(45) Date of Patent: May 9, 2023

(54) PORTABLE PERSONAL RESPIRATOR AND USE THEREOF

(71) Applicant: CLEANSPACE IP PTY LTD, Artarmon (AU)

(72) Inventors: Alexander Virr, Mangrove Mountain (AU); Dan Kao, Northbridge (AU); John Michael Snow, Killarney Heights (AU); Damian Charles Johnson, Fairlight (AU); Chayut Orapinpatipat, Chatswood (AU); Millen James Rath-May, Penshurst (AU)

(73) Assignee: CLEANSPACE IP PTY LTD., Artarmon (AU)

( * ) Notice: Subject to any disclaimer, the term of this patent is extended or adjusted under 35 U.S.C. 154(b) by 504 days.

(21) Appl. No.: 16/651,420

(22) PCT Filed: Sep. 13, 2018

(86) PCT No.: PCT/AU2018/050991
§ 371 (c)(1),
(2) Date: Mar. 27, 2020

(87) PCT Pub. No.: WO2019/060947
PCT Pub. Date: Apr. 4, 2019

(65) Prior Publication Data
US 2020/0282242 A1 Sep. 10, 2020

Related U.S. Application Data

(60) Provisional application No. 62/564,313, filed on Sep. 28, 2017.

(51) Int. Cl.
*A62B 7/10* (2006.01)
*A61M 16/00* (2006.01)
(Continued)

(52) U.S. Cl.
CPC .......... *A62B 7/10* (2013.01); *A61M 16/0051* (2013.01); *A61M 16/0057* (2013.01);
(Continued)

(58) Field of Classification Search
CPC .... A62B 7/00; A62B 7/10; A62B 7/12; A62B 9/006; A62B 9/00; A62B 18/006;
(Continued)

(56) References Cited

U.S. PATENT DOCUMENTS 5,740,795 A * 4/1998 Brydon ............... A61M 16/024
128/204.23
6,237,593 B1 5/2001 Brydon
(Continued)

FOREIGN PATENT DOCUMENTS

DE 102005054094 A1 6/2006
DE 202017003149 U1 8/2017
(Continued)

OTHER PUBLICATIONS

Dec. 23, 2021 Office Action issued in Chinese Application 202110642520.2.
(Continued)

*Primary Examiner* — Joseph D. Boecker
*Assistant Examiner* — Brian T Khong
(74) *Attorney, Agent, or Firm* — Oliff PLC (57) ABSTRACT

A respirator system includes a respirator with an air filter, a flow generator with a sensorless DC motor, a mask, a processor, a sensor, an electric power source, and a wireless transceiver. The respirator filters air, increase the pressure of the air, delivers the air to the mask at a pressure above ambient, gathers data with the sensor about operation of the respirator, and transmits the data. An intermediate electronic device is separate and remote from the respirator, and is configured to receive the transmitted data process the data,
(Continued)

and re-transmit the data. A computer receives the data, processes the data and generates at least one report regarding the respirator or a user of the respirator.

23 Claims, 9 Drawing Sheets

(51) Int. Cl.
*A61M 16/06* (2006.01)
*A61M 16/10* (2006.01)
*A62B 9/00* (2006.01)
*A62B 18/00* (2006.01)
*A62B 18/02* (2006.01)

(52) U.S. Cl.
CPC .......... *A61M 16/026* (2017.08); *A61M 16/06* (2013.01); *A61M 16/105* (2013.01); *A62B 9/006* (2013.01); *A62B 18/006* (2013.01); *A62B 18/025* (2013.01); *A61M 2016/0027* (2013.01); *A61M 2205/3317* (2013.01); *A61M 2205/3334* (2013.01); *A61M 2205/3365* (2013.01); *A61M 2205/3584* (2013.01); *A61M 2205/502* (2013.01); *A61M 2205/52* (2013.01); *A61M 2205/707* (2013.01); *A61M 2205/8206* (2013.01); *A61M 2209/088* (2013.01)

(58) Field of Classification Search
CPC ....... A62B 18/02; A62B 18/025; A62B 18/08; A62B 18/088; A61M 16/022; A61M 16/024; A61M 16/026; A61M 16/0051; A61M 16/0057; A61M 16/06; A61M 16/105

See application file for complete search history.

(56) References Cited

U.S. PATENT DOCUMENTS

| | | | | |
|---|---|---|---|---|
| 10,052,504 | B2* | 8/2018 | Volmer | A62B 7/10 |
| 2012/0138051 | A1 | 6/2012 | Curran et al. | |
| 2012/0174922 | A1 | 7/2012 | Virr et al. | |
| 2013/0312750 | A1* | 11/2013 | Farrugia | A61M 16/06 |
| | | | | 128/204.21 |
| 2014/0311490 | A1 | 10/2014 | Volmer et al. | |
| 2014/0373846 | A1 | 12/2014 | Kao et al. | |
| 2015/0136136 | A1 | 5/2015 | Fleming et al. | |
| 2016/0213955 | A1 | 7/2016 | Curran et al. | |
| 2016/0339200 | A1* | 11/2016 | Bath | A61M 16/16 |
| 2017/0028228 | A1 | 2/2017 | Zhao et al. | |
| 2017/0246486 | A1* | 8/2017 | Cazier | B01D 46/0047 |

FOREIGN PATENT DOCUMENTS

| | | |
|---|---|---|
| EP | 0518538 A2 | 12/1992 |
| EP | 2612688 A1 | 7/2013 |
| JP | H05-260786 A | 10/1993 |
| JP | 2002-199777 A | 7/2002 |
| JP | 2011-155802 A | 8/2011 |
| KR | 10-0956791 A | 3/2004 |
| RU | 2513773 C1 | 4/2014 |
| WO | 2011/006206 A1 | 1/2011 |
| WO | 2013/151944 A1 | 10/2013 |
| WO | 2016/157159 A1 | 10/2016 |
| WO | 2017/098329 A1 | 6/2017 |
| WO | 2017/136336 A1 | 8/2017 |
| WO | 2017/223438 A1 | 12/2017 |

OTHER PUBLICATIONS

Jul. 27, 2021 Search Report issued in Russian Application No. 2020114788.
Aug. 23, 2021 Office Action issued in Chinese Application No. 201880663805.7.
Feb. 3, 2021 Office Action issued in Chinese Patent Application No. 2018800638057.
May 19, 2021 Extended European Search Report issued in European Patent Application No. 18863195.6.
Jan. 26, 2022 Office Action issued in Chinese Application No. 201880063805.7.
Dec. 20, 2018 International Search Report issued in Australian Application No. PCT/AU2018/050991.
Dec. 20, 2018 Written Opinion issued in Australian Application No. PCT/AU2018/050991.
Jun. 30, 2022 Office Action issued in Korean Application No. KR-2020-7009012.
Aug. 2, 2022 Office Action issued in Japanese Application No. 2020-518472.

* cited by examiner

PORTABLE PERSONAL RESPIRATOR AND USE THEREOF

BACKGROUND

For the general public, protection from pollution and disease in their daily life relies largely on dust or surgical marks. However, these masks only provide basic protection, due to leakage around the masks, even when the filter material used in making such masks is typically labeled as suitable for high efficiency filtering. Due to the extra resistance imposed by the filter media, the user has to breathe considerably harder than they normally do without the mask. Thus, it is quite difficult for anyone to use such a mask comfortably for a prolonged period. Furthermore, $CO_2$ and moisture accumulate inside the mask, which tends to make the situation worse. In addition, the higher the efficiency of the filter media, the higher the flow resistance it will impose, thus making these masks even more uncomfortable for prolonged use. Such effects are particularly obvious for those who have weak or impaired respiratory systems, such as elderly people, children, and the sick, such as asthma and COPD patients.

Dust and surgical masks have therefore been widely used by general public largely because of their ease of use and the fact that there are not any acceptable powered air purifying respirator (PAPR) solutions available should anyone wish to use a more efficient and comfortable device.

However, it is apparent that the air quality in many everyday situations can be very poor. In larger cities, the heavy density of cars, buses, trucks and motorcycles often emit excessive amounts of toxic pollutants. Power plants are another key source of pollutions. Natural or man-made disasters, such as sandstorms, fires of any kinds, also contribute harm to people's respiratory systems. Those pollutions include dust (suspended particles), lead, and harmful gases such as $NO_2$, $SO_2$, CO, $O_3$, VOCs, smoke, etc. Long term exposure to these pollutions is evidenced to be harmful and often causes life threatening diseases. SARS, bird and swine influenza, three of the most recent disease-related threats to humans are also pollutants, or air borne diseases, and are potentially deadly to human beings.

A protection device that offers the similar level of protection and comfort and yet can also be acceptable to use by ordinary people or light industrial/professional users is clearly needed.

U.S. Patent Application Publication No. 2012/0174922 to Virr et al., which is hereby incorporated by reference in its entirety, discloses a breathing apparatus including a mask and a neck component. The mask is adapted to substantially surround at least the mouth or nostrils of a user. The neck component is attached to said mask, and adapted to substantially surround the back of the neck of said user. The neck component includes a flow generator to receive unfiltered air from a surrounding environment, filter said unfiltered air, and, provide filtered air to said mask. The breathing apparatus has a low profile appearance compared to prior devices and is adapted to sit comfortably about the neck of the user.

U.S. Patent Application Publication No. 2014/0373846 to Kao et al., which is hereby incorporated by reference in its entirety, discloses powered air purifying respirators generally for use in polluted environments. The powered air purifying respirators includes a powered impellor arranged to draw air from the atmosphere, a filter element and a mask to provide the filtered and pressurized air to the user. The powered air purifying respirators include a generator unit with a filter and impellor for pressurizing the air, behind the head of the user, and include components for improving delivery of the air to the user and improving its quality.

BRIEF SUMMARY

The devices described in U.S. Patent Application Publication No. 2012/0174922 and U.S. Patent Application Publication No. 2014/0373846 included significant advances in the art. However, further advancements in areas such as size reduction, data gathering and analysis of gathered data are desirable. This application discloses such desirable advancements and/or seeks to overcome the deficiencies of the prior art.

In an example, a respirator system comprises a respirator including an air filter, a flow generator with a sensorless DC motor, a mask, a processor, a sensor, an electric power source, and a first wireless transceiver, wherein the respirator is configured to draw ambient air through the air filter, increase the pressure of the air, deliver the air to the mask at a pressure above ambient, gather data with the sensor about operation of the respirator, and transmit the data with the first wireless transceiver; an intermediate electronic device comprising a processor, a memory, a second wireless transceiver and a first network transceiver, wherein the intermediate electronic device is separate and remote from the respirator, and the intermediate electronic device is configured to receive the data transmitted by the first wireless transceiver, process the data, and re-transmit the data with the first network transceiver; and a computer with a second network transceiver, a processor, and a memory storing instructions that, when executed, cause the computer to receive the data, process the data and generate at least one report regarding the respirator or a user of the respirator.

In an example, a respirator system comprises a respirator including a filter, a motor, a first data transceiver and a first processor, wherein the first processor is configured to determine a flow rate through the respirator using steady state motor power and a predetermined characterization of the respirator, and to cause the first data transceiver to transmit data corresponding to the flow rate and a pressure in the respirator; and an electronic device including a second data transceiver and a second processor, wherein the second processor is configured to read the data after receipt of the data by the second data transceiver and determine a state of the respirator using the data.

In an example, a method of determining a state of a respirator that includes a filter and a motor, the method comprises calculating a flow rate through the respirator using steady state motor power and a predetermined characterization of the respirator; transmitting data corresponding to the flow rate and a pressure in the respirator; receiving the data with an electronic device; and determining a state of the respirator using the data and the electronic device.

Other aspects, features, and advantages of this technology will become apparent from the following detailed description when taken in conjunction with the accompanying drawings, which are a part of this disclosure and which illustrate, by way of example, principles of this technology.

DETAILED DESCRIPTION

The following description is provided in relation to several examples which may share common characteristics and features. It is to be understood that one or more features of any one example may be combinable with one or more features of the other examples. In addition, any single feature or combination of features in any of the examples may constitute additional examples.

Figure 1:
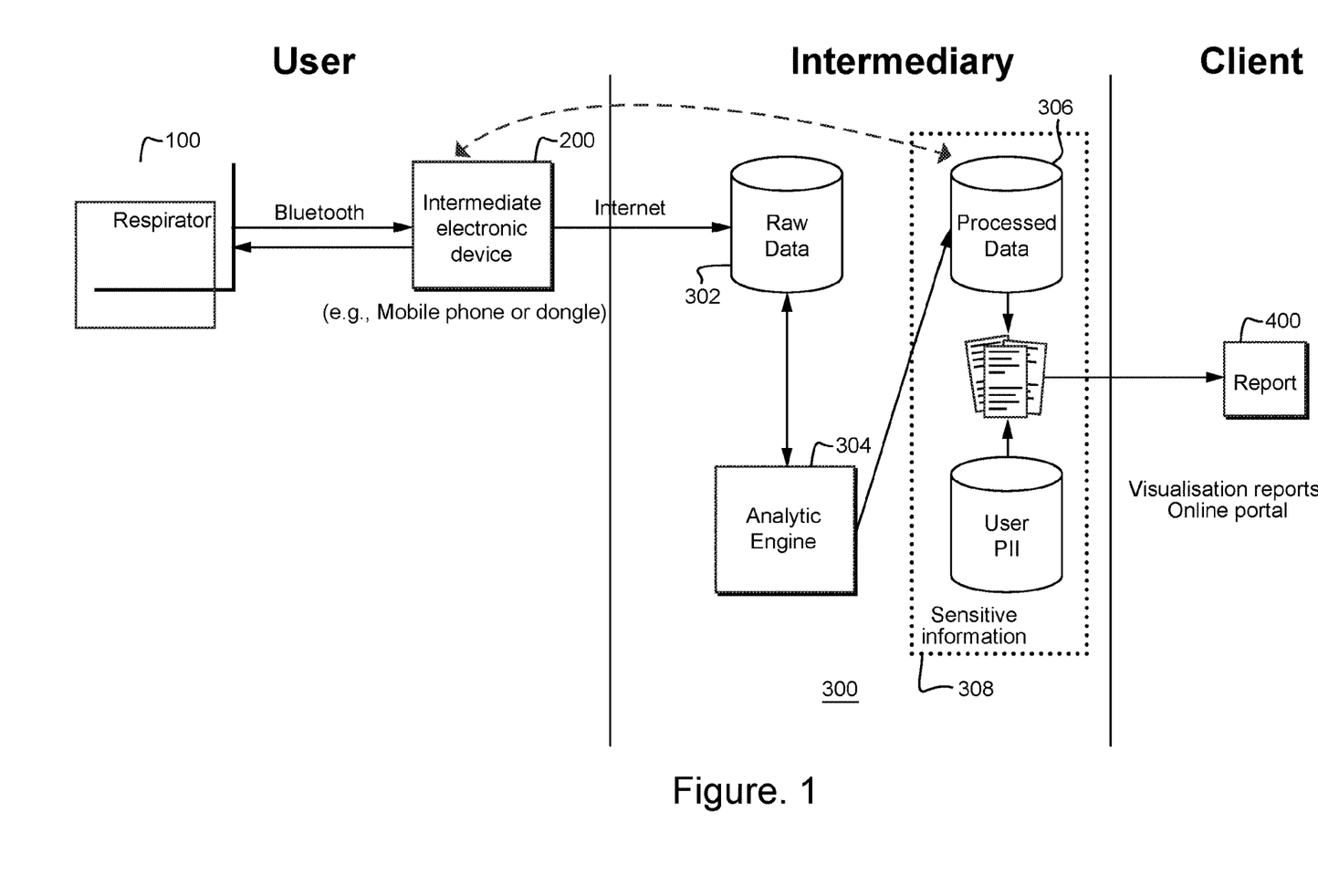
FIG. 1 is a system architecture according to the present technology.

FIG. 1 illustrates an embodiment of a system architecture with a respirator 100, an intermediate electronic device 200, an intermediary 300 for remote data processing, and generated reports 400. The respirator 100 communicates with the intermediate electronic device 200, preferably with wireless communication, although wired communication may be used as well. Relatively short range wireless communication, such as Bluetooth®, may be desirable between the respirator 100 and intermediate electronic device 200 because of its relatively low power consumption and wide availability. The intermediate electronic device 200 may be a mobile phone or some other device such as a dongle, which may be attached to a general purpose computer or to the respirator. Mobile phones may be advantageous because of their wide availability, flexibility (through downloadable applications), and ability to communicate via multiple wireless protocols such as Bluetooth® and Wi-Fi and over cellular networks. A dongle or similar device may be advantageous if a mobile phone is not available or undesirable in a particular location. For example, if privacy or data security at the worksite is sufficiently important, a dongle may be more desirable than a mobile phone. A dongle may be less complex than a mobile phone. For example, a dongle may have communication and memory capabilities but relatively limited processing capabilities.

The respirator 100 transmits data to the intermediate electronic device 200. Use of an intermediate electronic device 200 may reduce at least one of the cost, complexity, weight and power consumption of the respirator 100. Higher level computer processing, greater memory and longer range data transmission can be integral aspects of the intermediate electronic device 200. Thus the respirator 100 need only include components related to data acquisition and monitoring that either must be located in the respirator 100 to function or that are not included in the intermediate electronic device 200—sensors (e.g., pressure sensors) being examples of both. Also, a mobile phone may already be carried by the user of the respirator 100. Utilizing a mobile phone as the intermediate electronic device 200 may provide an efficient use of an underutilized computing source and would not require equipment that is not already nearby or being carried by the user.

When the data is transmitted to the intermediate electronic device 200, at least two alternatives may occur. First, the intermediate electronic device 200 may pass the data along in raw form to the intermediary 300 via the internet for remote data processing. In this scenario, all data processing would occur at the intermediary 300. Second, the intermediate electronic device 200 may process some or all of the data before transmission to the intermediary 300. Of course, both raw data and processed data may be transmitted from the intermediate electronic device 200 to the intermediary 300. Whether the data is sent in raw form or processed before sending may be determined based on factors such as data rates, battery life and usefulness of immediate feedback to the user of the processed data.

At the intermediary 300, the raw data 302 is processed by an analytic engine 304. The analytic engine 304 may include software or other logic operated on a general purpose computer or server. After processing by the analytic engine, the raw data 302 may be transformed into processed data 306. Various types of data and the way in which it can be processed is discussed further below. Once the data is processed, it may be used to generate reports 400. The generation of the reports 400 may utilize other data, such as user specific data or data from other respirators, that is separate from the raw data 302 or processed data 306. For example, user specific data could include physiological parameters of the user that, when combined with the processed data, could be used to make predictions or analysis related to the health of the user. This type of data may be considered sensitive information 308 by a particular legal jurisdiction or the user, and such sensitive information 308 may require higher or different levels of security. Data from other respirators may combined to provide planning for maintenance, repairs, spare parts ordering, distribution of assets, etc. This type of data may be proprietary company information that also causes the data to be sensitive information 308. The reports 400 may provide visualization of the processed data 306 and/or be an online portal for viewing the processed data 306. Exchange of processed data 306 may occur between the intermediate electronic device 200 and the intermediary 300 in either direction. For example, if the intermediate electronic device is used to process some or all of the data, the analytic engine 304 may be bypassed. Or, some processed data 306 may be sent back to the intermediate electronic device 200 for use by the user.

Figure 2:
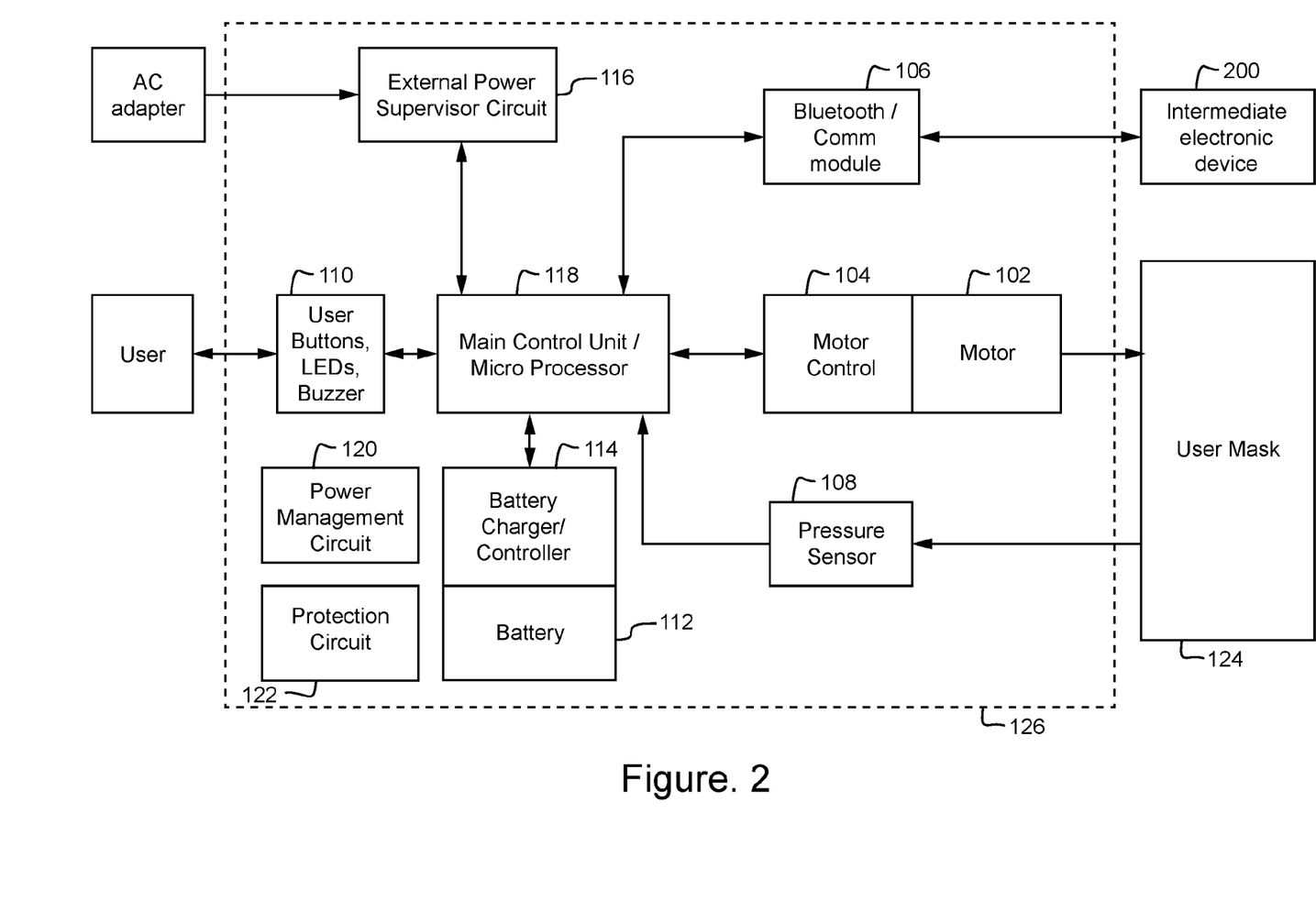
FIG. 2 is a system diagram of a respirator according to the present technology.

FIG. 2 is a system diagram that includes embodiments of components of the respirator 100 and components that interact with the respirator 100. The respirator 100 may include a motor 102, a motor control 104, a communication module 106, a pressure sensor 108, a user interface 110, a battery 112 (an example of an electric power source), a battery charge/control circuit 114, an external power supervisor circuit 116, a main control unit 118, a power management circuit 120, a protection circuit 122 and user mask 124. The motor 102 is preferably a sensorless DC motor that drives an impeller of a flow generator.

The system can measure mask pressure around 100 times per second (100 Hz). The main control unit 118 may continually (e.g., at a frequency of 100 Hz) adjust motor (and thus an associated flow generator) speed with the aim of keeping mask pressure at a target value, typically around 10 mm $H_2O$.

To control a sensorless DC motor, the CPU preferably monitors the following parameters (also at 100 Hz): motor speed, motor current, battery voltage, and temperature within the respirator 100.

The respirator continually (100 Hz) writes a data stream to the communication module 106. This stream may include motor speed, motor current, mask pressure and battery voltage.

The communication module 106 may include Bluetooth®, which may be used to communicate with the intermediate electronic device 200. The respirator may write its serial data stream, over Bluetooth, to the intermediate electronic device 200. It may also write a lower-frequency data stream consisting of summary statistics calculated once per breath, for instance breath duration, minimum and maximum motor speeds, and various parameters such as how long mask pressure is maintained below some threshold value.

In come embodiments, communication can be in both directions between the respirator 100 and the intermediate electronic device. The intermediate electronic device 200, which may include an application running on a mobile phone, may have the ability to write data into the memory of the respirator 100. The intermediate electronic device 200 may also assume control of the motor 102, for instance ordering it to maintain some constant motor speed or mask pressure, or any other behavior as required.

The intermediate electronic device 200, particularly if it is a mobile phone, may have access to the user's current location (latitude, longitude and altitude) from a the GPS.

In at least one embodiment, the respirator 100 may include a sensor (such as a magnetic sensor) to detect when the filter is missing and when it has been changed and/or removed and replaced. The sensor in the respirator may read one or more magnets in the filter, where removal of the magnetic field indicates removal and/or replacement of the filter.

With one or more of the components discussed above, one or more of the following calculations may be performed.

Figure 3A:
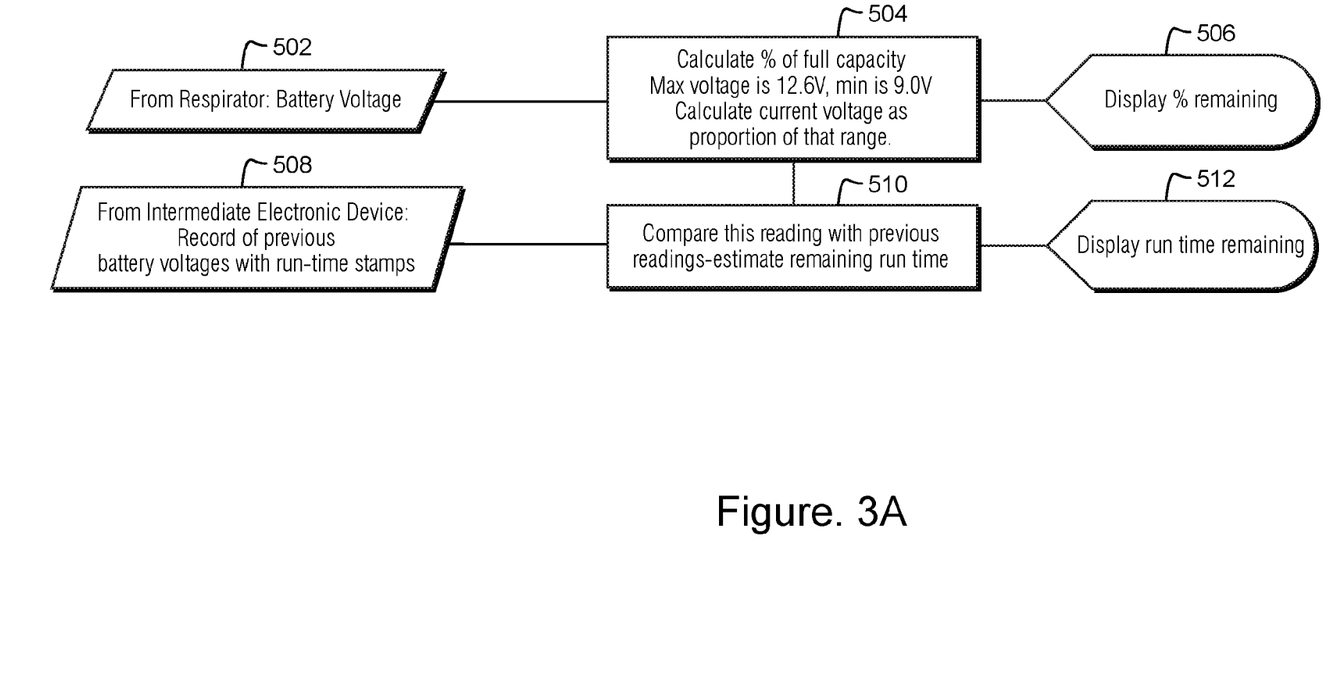
FIGS. 3A and 3B illustrate various calculations and operations related to a battery.
Figure 3B:
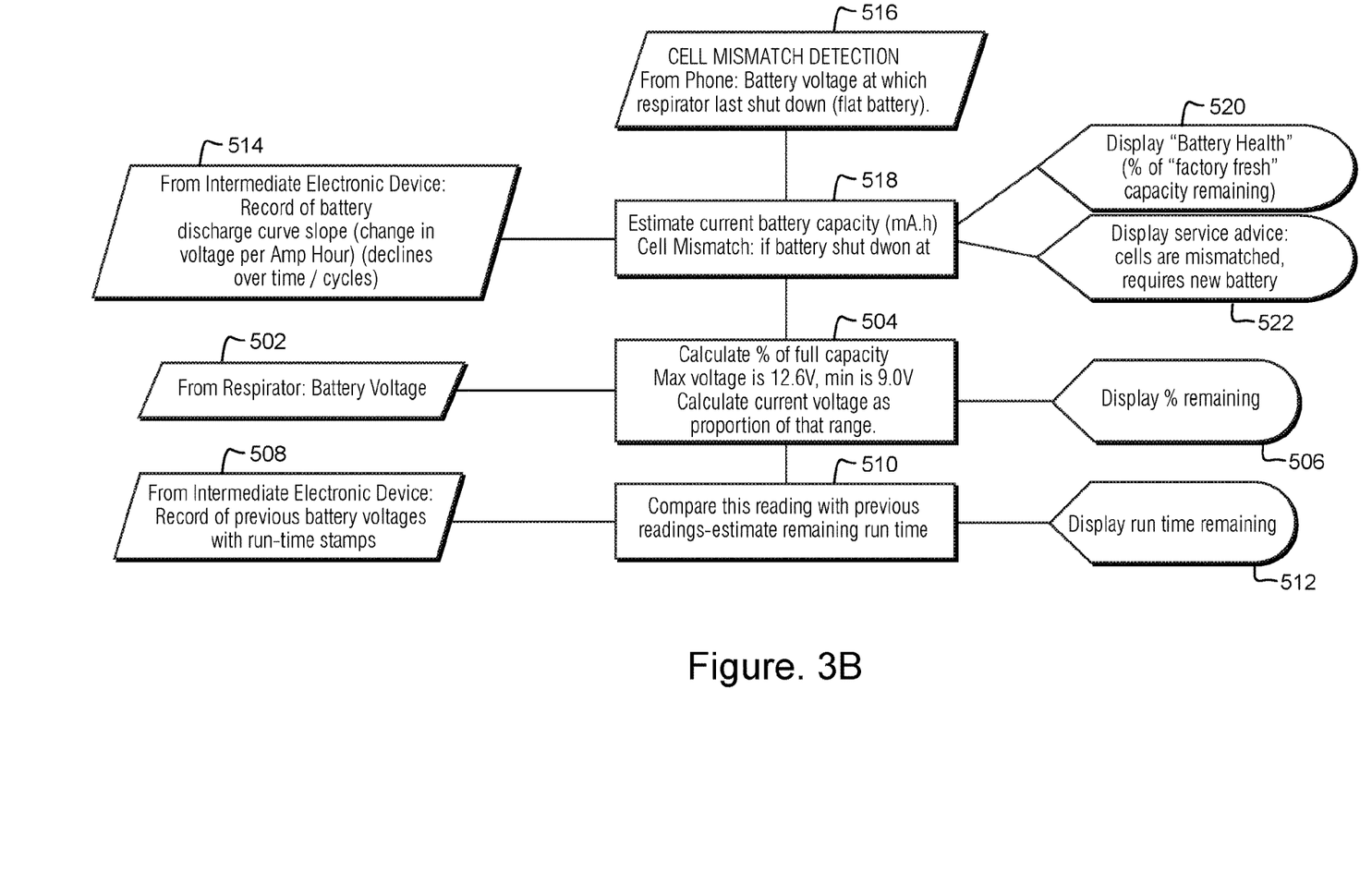

FIGS. 3A and 3B illustrate various calculations and operations related to the battery 112.

At 502 in FIG. 3A, an embodiment of the respirator 100 can determine the battery voltage. At 504, the percentage of the battery capacity remaining can be determined. For example, if the maximum battery voltage is 12.6V and the minimum voltage is 9.0V, the current voltage can be determined as a proportion of that range. This calculation could occur at the respirator 100 or the intermediary 300, but is preferably calculated at the intermediate electronic device 200, particularly if the intermediate electronic device 200 is a mobile phone. At 506, the percentage of battery remaining can be displayed, which may suggest that a mobile phone is preferable as the intermediate electronic device 200 because of the built in display.

At 508, a record of previous battery voltages at different time stamps can be accessed. At 510, a previous battery voltage and time stamp can be compared to a prior battery voltage reading and time stamp. By comparing the differences in battery voltage and time, an estimate of remaining running time can be generated. This calculation could occur at the respirator 100 or the intermediary 300, but is preferably calculated at the intermediate electronic device 200, particularly if the intermediate electronic device 200 is a mobile phone. At 512, the run time remaining can be displayed, which may suggest that a mobile phone is preferable as the intermediate electronic device 200 because of the built in display.

FIG. 3B is similar to FIG. 3A, but includes some additional steps. Only the additional steps are described. At 514, an embodiment of the intermediate electronic device 200 can access a record of battery discharge. This may be in the form of change in voltage per amp-hour, or a decline in voltage over time or a decline in voltage per cycle. At 516, the intermediate electronic device 200 can determine a recorded battery voltage at which the respirator 100 last shut down due to insufficient power. At 518, the data determined at 514 and 516 can be compared to generate an estimate of current battery capacity (e.g., in milliamp-hours). A determination of battery health, which can be a percentage of battery capacity remaining versus original battery capacity, can be performed. This determination could occur at the respirator 100 or the intermediary 300, but is preferably calculated at the intermediate electronic device 200, particularly if the intermediate electronic device 200 is a mobile phone. At 520, a battery health factor can be displayed, which may suggest that a mobile phone is preferable as the intermediate electronic device 200 because of the built in display.

In some embodiments, if the respirator 100 shut down due to insufficient power at a different battery voltage than a prior shutdown, a determination can be made that there is a cell mismatch in the battery. This determination could occur at the respirator 100 or the intermediary 300, but is preferably calculated at the intermediate electronic device 200, particularly if the intermediate electronic device 200 is a mobile phone. At 522, a battery health factor can be displayed, which may suggest that a mobile phone is preferable as the intermediate electronic device 200 because of the built in display.

Figure 4:
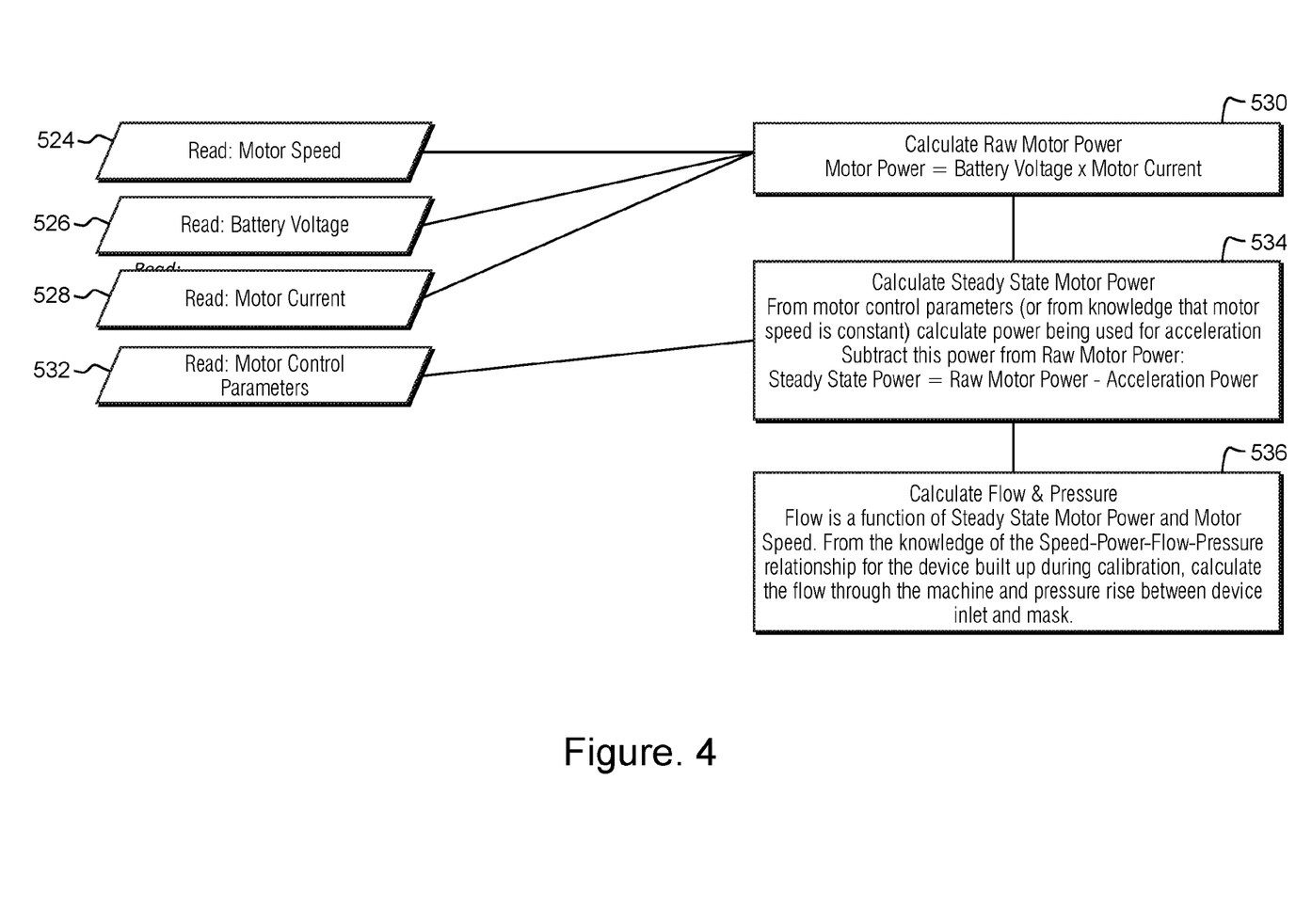
FIG. 4 illustrates an algorithm for calculating flow through a respirator.

FIG. 4 illustrates an algorithm for calculating flow through the respirator 100 at least during inhalation. This calculation may be able to be performed entirely in the respirator. At 524, the motor speed is determined. At 526, the battery voltage is determined. At 528, the motor current is determined. At 530, the raw motor power is calculated by multiplying the battery voltage and motor current. At 532, the motor control parameters are determined. At 534, the steady state motor power is determined From motor control parameters, the power being used for acceleration of the motor can be calculated. If the motor speed is constant, then the acceleration power will be zero. The steady state motor power can be determined by subtracting acceleration power from raw motor power. At 536, the flow and pressure can be determined. Flow is a function of steady state motor power and motor speed for a given flow generator. During manufacture, each respirator can be attached to a test jig consisting of a flow meter, a flow control valve, a pressure meter and a computer connected to a serial communication port of the respirator. The respirator is then exercised through multiple (e.g., 100) speed-flow points (for instance 25000 rpm-100 liters per minute). At each speed-flow point the mask pressure, motor current and battery voltage are recorded without a filter in the respirator. The output of this calibration process is a family of data points or curves which relate flow to motor speed and motor power. Thus at any time when running, the flow through the flow generator, and thus the respirator, can be calculated using a knowledge of the instantaneous motor speed and motor power. The same calculation also yields the current pressure differential generated by the respirator (e.g., from device inlet—i.e. directly behind the filter—to the interior of the mask).

With an embodiment of this method of determining flow and pressure, simplification and cost reduction of the respirator 100 may be able to be achieved. This method may allow for use of a sensorless DC motor and elimination of a flow meter. Flow meters usually include a sensitive pressure transducer monitoring the pressure change across some constriction in the system. This type of flow meter is accurate but expensive as it requires an additional pressure transducer. But with an embodiment of the method described above, the pressure transducer and constriction may not be required. Thus a flow meter, in the traditional sense, may be able to be omitted.

Figure 5A:
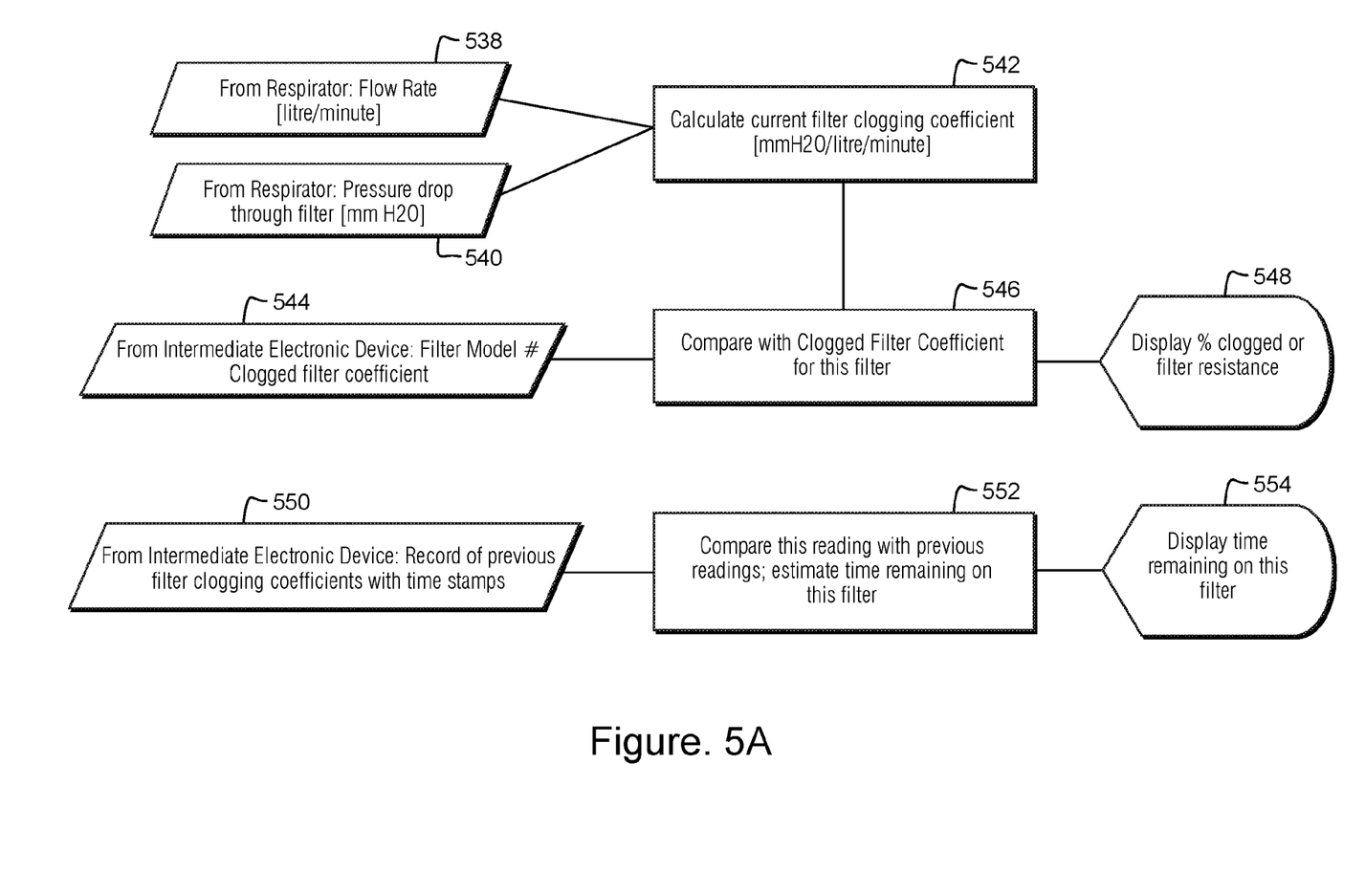
FIGS. 5A and 5B illustrate an algorithms for determining a state of a filter.

FIG. 5A illustrates an algorithm for determining a state of a filter. At 538, the flow rate through the respirator is determined. The flow rate may be able to be determined by the respirator 100. At 540, the pressure drop through the filter is measured in the respirator. Such measurement may be by way of a pressure transducer in the respirator 100. At 542, a current filter clogging coefficient is calculated. This can be calculated by dividing the pressure drop through the filter measured at 540 by the flow rate determined at 538. An exemplary unit of measure for the current clogging coefficient is mm $H_2O$/liter/minute. At 544, a clogged filter coefficient is read from a memory, such as a memory in the intermediate electronic device or at the intermediary 300. The clogged filter coefficient is preferably determined in advance, and can be determined based upon testing in a laboratory or as a result of use in the field. The clogged filter coefficient preferably has the same unit of measure as the current clogging coefficient. At 546, the current clogging coefficient is compared to the clogged filter coefficient to determine the relative amount that the filter is clogged. At 548, the clogging percentage or filter resistance is displayed, which may suggest that a mobile phone is preferable as the intermediate electronic device 200 because of the built in display.

Based on the current filter clogging coefficient determined at 542, an estimate of remaining filter life may be able to be determined. At 550, a previous current filter clogging coefficient, along with a time stamp, can be accessed. At 552, the current value and the prior value are compared. Based on the percentage of life changed and time between values, and estimate of the time of use remaining for the filter can be determined. At 554, the time remaining on the filter can be displayed, which may suggest that a mobile phone is preferable as the intermediate electronic device 200 because of the built in display.

Figure 5B:
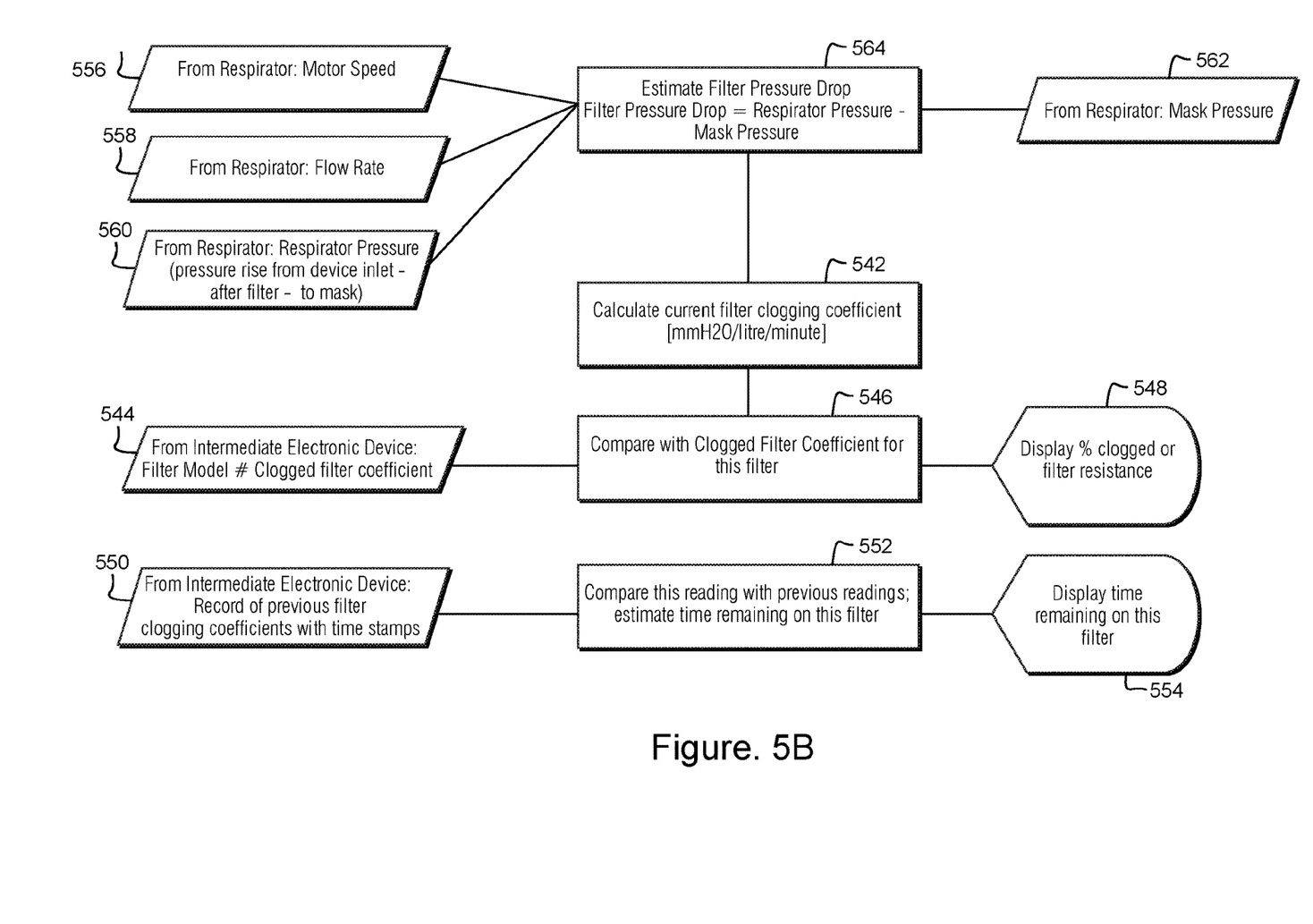

An alternate filter state algorithm is illustrated in FIG. 5B. This algorithm differs from the algorithm in FIG. 5A in that pressure drop across the filter is estimated instead of being measured.

At 556, the motor speed is determined. At 558, the flow rate is determined (see, e.g., refs. 524-536 and associated descriptions above). At 560, the respirator pressure (e.g., pressure rise from downstream of the filter to the mask) is determined. At 562, the mask pressure is measured by the respirator 100. At 564, the filter pressure drop is estimated by subtracting mask pressure from the respirator pressure. Refs. 542-554 are the same as for FIG. 5A and their description is not repeated here.

Figure 6:
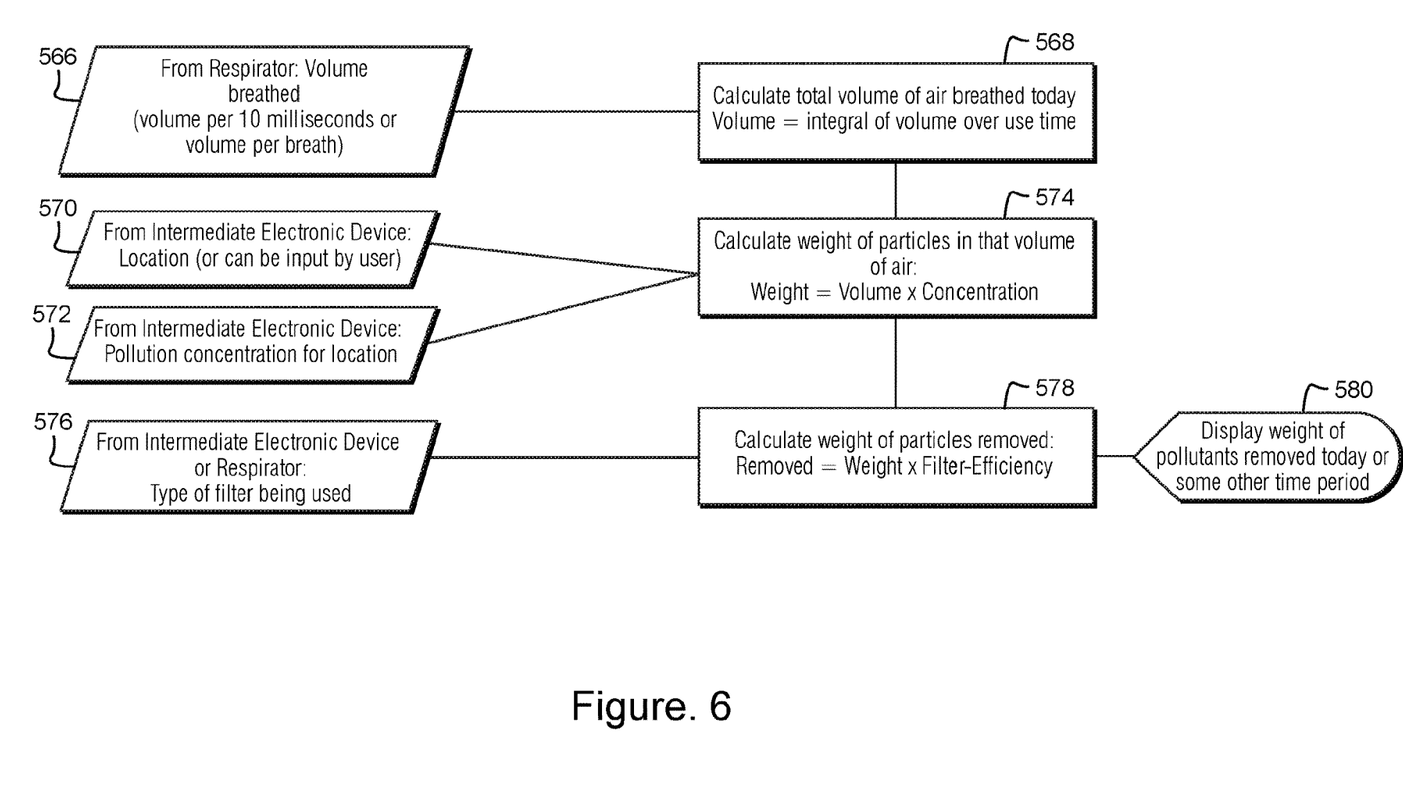
FIG. 6 illustrates an algorithm for determining particulates removed by a respirator.

FIG. 6 illustrates an algorithm for determining particulates removed by the respirator 100. At 566, a volume breathed is determined, which could be volume per 10 milliseconds, volume per breath, or any other suitable representation of volume breathed. This can be determined by the respirator as discussed above with respect to FIG. 4. At 568, a total volume breathed is calculated. The total volume breathed can be determined by calculating the integral of volume breathed over time, and can be calculated for a given period of use (such as one day). At 570, the location of the respirator 100 is determined. The location can be input by a user or determined automatically by a locating system (such as a GPS or other locating system that may be found in a mobile phone) and the location data can be added to, or sent with, any data transmitted by the intermediate electronic device 200. The location data may also be transmitted alone.

At 572, the pollution concentration for the location of the respirator is determined. This can be determined, for example, by the intermediate electronic device 200 or intermediary 300 retrieving pollution data from a database, remote measuring system or the like. At 574, the weight of particles can be calculated by multiplying the total volume breathed with the pollution concentration. At 576, the type of filter being used in the respirator 100 is determined, along with performance data of the filter. This information can be stored, for example, in the intermediate electronic device 200. Of course, this information could also be stored in any other suitable location, such as the respirator 100 or by the intermediary 300. At 578, the weight of particles removed is calculated by multiplying a filter efficiency with the weight of particles. At 580, the weight of pollutants removed for the given time period is displayed. This can be displayed at the intermediary device, which may suggest that a mobile phone is preferable as the intermediate electronic device 200 because of the built in display, or as part of a report 400. This algorithm may be significantly more accurate than prior methods in which the volume breathed is inferred from an earlier laboratory test. In other words, accuracy can be gained by actual measurement of breathing during use.

The percentage that the filter is clogged, the time remaining on filter, and the amount of pollutants removed are each examples of the state of a respirator.

A model or part number of a filter and/or the filtration coefficient of a filter are examples of a predetermined value associated with the filter.

The type of control of the respirator (fast, ultra-responsive) measures a range of parameters (mask pressure, motor speed, motor current, battery voltage, etc.) at a frequency which mirrors the rate at which physical changes occur in the mask. For instance, leaks may develop and re-seal over a period of fractions of a second; physiologically-significant changes in the breathing of the user will be marked by changes in flow rate that happen over a 300-500 ms period of inhalation. Thus the respirator 100 may be controlled at a rate that also allows detection of changes in the flow pattern from the mask (e.g. leak) or in the breathing pattern of the user (e.g. exhaustion, shortness of breath, flow limitation, lung capacity, etc.). Knowledge of mask pressure (plus one or more of the other parameters mentioned) may be used to directly estimate leak into the mask (and consequently the "fit" or "protection factor" of the mask).

For example, using the algorithm of FIG. 6, the amount of particles that are not filtered can also be determined. This may be correlated to a protection factor, e.g., the ratio of the particle concentrations inside and outside the mask. Also the use of this method of estimation may assess protection factor continuously (every breath during use) instead of as part of some once-per-year test using specialized equipment. Prior systems may use a method to assess mask fit based on the decay of vacuum in a mask. The present technology differs in that (1) the normal mask pressure is measured, not a vacuum that has been specially generated for test purposes, (2) no additional adaptors or monitoring equipment are required, and (3) pressure may be measured continuously and at high frequency, whereas the vacuum test measurement is based on one long pressure decay.

With the calculation, communication and/or storage capability of the intermediate electronic device 200 and/or intermediary 300, a flow of data can occur from the respirator 100 to the cloud or a specific computer or server. This may allow for data analytics of an individual respirator 100 (and/or the associated user) or a collection of respirators. This may allow for calculations such as breathing rates; minute volume; breathing volumes; breathing exertion; fatigue levels and warnings; distressed levels; benchmarking against other units; alerts for servicing or equipment issues; alerts and reminders for filter changes; continuous and automatic monitoring and notification of equipment performance and service notification; alerts for unit operating outside recommended range; amount of hazards filtered by use or per hour or over time; pressures; temperatures; battery load and battery use; battery condition/life; filter load; filter resistance; filter performance; motor performance and failure; measurement of protection factor; mask and system fit in real time; use and compliance over time per user; real time data to the user via mobile phone app (equipment check, protection, performance); filter recommendations based on load over time; data of longitudinal studies such as wearer health, equipment performance, sports, etc.; health diagnostics: breathing patterns and prediction of breathing pathologies or acute breathing changes; flow limitation; change of breathing pattern over time; sports or fitness performance, and consumer pollution. Also, actions such as the ability to write data into the respirator (e.g., last filter load, type of filter) may occur.

Figure 7:
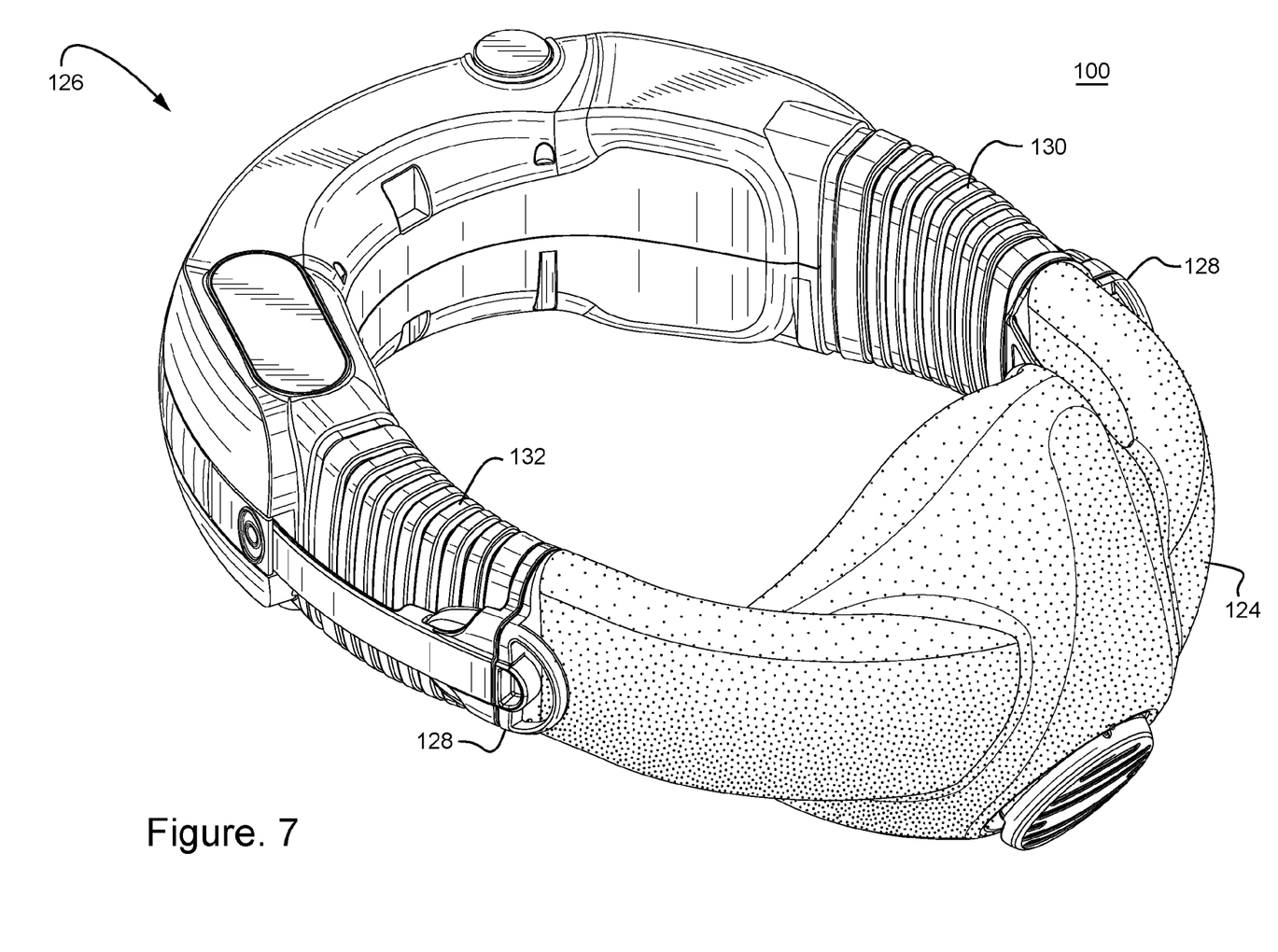
FIG. 7 illustrates an exemplary respirator.

FIG. 7 is an illustration of an exemplary respirator 100 suitable for performing the methods above, and may include features described with respect to FIG. 2. The user mask 124 is an exemplary mask that covers a user's nose and mouth. Other mask types may be employed that cover more or less of the user's face. For example, the mask could cover only the nose or the mouth. Or the mask could also include covering for the user's eyes. The mask is removable at the connectors 128.

The rear portion 126 of the respirator 100, in some embodiments, may include all of the components included within the corresponding dashed line of FIG. 2. As the mask 124 is removable from the rear portion 126, the rear portion 126 is, in a functional sense, the respirator 100 and the mask 124 is a user interface for use with the respirator.

The respirator 100 includes a left arm 130 and a right arm 132. In some embodiments, only one of the arms is used for flow to the mask 124 and includes a flow duct, and the other arm provides a pressure sense line that is substantially the same size as the arm used for flow (a non-flow duct). Although a much smaller pressure sense line could be used, it has been found that in at least one embodiment, having only one arm, or one arm that is much smaller than another, is not well received by users, but having a pressure sense line that is the same size as the flow line may be advantageous. For example, a pressure sensor can be located in the rear portion 126, which is relatively far away from the mask 124, yet still measure pressure, and pressure changes, at the mask 124 substantially instantaneously. Mask pressure is effectively read directly at the mask, via the non-flow duct, rather than inferred from a reading of pressure near the fan outlet. Including a pressure sensor at the mask could also avoid the need to infer pressure by reading of pressure near the fan outlet, but this may introduce complexities and expense associated with including a pressure transducer in the mask 124, such as additional electrical connections.

While the present technology has been described in connection with several practical examples, it is to be understood that the technology is not to be limited to the disclosed examples, but on the contrary, is intended to cover various modifications and equivalent arrangements included within the spirit and scope of the technology.

In this specification, unless the context clearly indicates otherwise, the word "comprising" is not intended to have the exclusive meaning of the word such as "consisting only of", but rather has the non-exclusive meaning, in the sense of "including at least". The same applies, with corresponding grammatical changes, to other forms of the word such as "comprise", etc.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Any promises made in the present document should be understood to relate to some embodiments of the invention, and are not intended to be promises made about the invention in all embodiments. Where there are promises that are deemed to apply to all embodiments of the invention, the applicant/patentee reserves the right to later delete them from the description and they do not rely on these promises for the acceptance or subsequent grant of a patent in any country.

The invention claimed is:

1. A respirator system comprising:
a respirator including an air filter, a flow generator with a sensorless DC motor, a mask, a first processor configured to monitor motor speed, motor current, and electric power source voltage, a pressure sensor configured to measure pressure of air at the mask, an electric power source, and a first wireless transceiver, wherein the respirator is configured to draw ambient air through the air filter, increase the pressure of the air, deliver the air to the mask at a pressure above ambient, gather mask pressure with the pressure sensor, and transmit data that includes the motor speed, the motor current, the mask pressure and the electric power source voltage with the first wireless transceiver;
an intermediate electronic device comprising a second processor, a memory, a second wireless transceiver and a first network transceiver, wherein the intermediate electronic device is separate and remote from the respirator, and the intermediate electronic device is configured to receive the data transmitted by the first wireless transceiver, process the data, and re-transmit the data with the first network transceiver; and
a computer with a second network transceiver, a third processor, and a second memory storing instructions that, when executed, cause the computer to receive the data, process the data and generate at least one report regarding the respirator or a user of the respirator, wherein the report includes a flow rate through the filter that is calculated using the motor speed, the motor current, the mask pressure and the electric power source voltage.

2. The respirator system according to claim 1, wherein the motor speed, the motor current, and the electric power source voltage are used to determine steady state motor power, which is raw motor power minus acceleration motor power.

3. The respirator system according to claim 1, wherein the respirator does not include a flow sensor.

4. A respirator system comprising:
a respirator including an air filter, a flow generator with a sensorless DC motor, a mask, a first processor configured to monitor motor speed, motor current, and electric power source voltage, a pressure sensor configured to measure pressure of air at the mask, an electric power source, and a first wireless transceiver, wherein the respirator is configured to draw ambient air through the air filter, increase the pressure of the air, deliver the air to the mask at a pressure above ambient, gather mask pressure with the pressure sensor, and transmit data that includes the motor speed, the motor current, the mask pressure and the electric power source voltage with the first wireless transceiver;

an intermediate electronic device comprising a second processor, a memory, a second wireless transceiver and a first network transceiver, wherein the intermediate electronic device is separate and remote from the respirator, and the intermediate electronic device is configured to receive the data transmitted by the first wireless transceiver, process the data, and re-transmit the data with the first network transceiver; and a computer with a second network transceiver, a third processor, and a second memory storing instructions that, when executed, cause the computer to receive the data, process the data and generate at least one report regarding the respirator or a user of the respirator, wherein the report includes a recommendation to replace the filter based on a flow rate through the filter that is calculated using the motor speed, the motor current, the mask pressure and the electric power source voltage.

5. The respirator system according to claim 4, wherein the motor speed, the motor current, and the electric power source voltage are used to determine steady state motor power, which is raw motor power minus acceleration motor power.

6. A respirator system comprising:

a respirator including a filter, a motor, a first data transceiver and a first processor, wherein the first processor is configured to determine a flow rate through the respirator using steady state motor power and a predetermined characterization of the respirator, and to cause the first data transceiver to transmit data corresponding to the flow rate and a pressure in the respirator; and an electronic device including a second data transceiver and a second processor, wherein the second processor is configured to read the data after receipt of the data by the second data transceiver and determine a state of the respirator using the data.

7. The respirator system according to claim 6, wherein the respirator comprises an electric power source and the first processor is configured to determine a speed of the motor, a voltage of the electric power source, and a current of the motor, and determine the steady state motor power using the speed, the voltage and the current.

8. The respirator system according to claim 7, wherein the steady state motor power is raw motor power minus acceleration motor power.

9. The respirator system according to claim 8, wherein the first processor is configured to determine the acceleration motor power from at least one of a control parameter of the motor and a rate of change of the speed of the motor.

10. The respirator system according to claim 8, wherein the first processor is configured to determine the raw motor power using the voltage of the electric power source and the current of the motor.

11. The respirator system according to claim 6, wherein the predetermined characterization of the respirator correlates the steady state motor power with the flow rate.

12. The respirator system according to claim 6, wherein the predetermined characterization of the respirator is an equation stored in the respirator.

13. The respirator system according to claim 6, wherein the predetermined characterization of the respirator is a lookup table stored in the respirator.

14. The respirator system according to claim 6, wherein the second processor is configured to determine remaining useful life of the filter and generate instructions to display the remaining useful life.

15. The respirator system according to claim 14, wherein the remaining useful life is a percentage of clogging that is calculated using the pressure in the respirator, the flow rate, and a predetermined value associated with the filter.

16. The respirator system according to claim 14, wherein the electronic device is configured to store a clogging coefficient calculated using a pressure drop through the filter, the flow rate, and a predetermined value associated with the filter, and determine the remaining useful life as a length of time based on a comparison between a present value of the clogging coefficient and a stored value of the clogging coefficient.

17. The respirator system according to claim 6, wherein the respirator includes a mask, and one of the first processor and the second processor is configured to estimate a pressure drop through the filter using the flow rate, a speed of the motor, and a pressure in the mask.

18. The respirator system according to claim 6, wherein the state of the respirator is a weight of particles removed by the filter.

19. The respirator system according to claim 18, wherein the weight of particles is determined using the flow rate, a location of the respirator and a pollution concentration for the location of the respirator.

20. The respirator system according to claim 6, wherein the electronic device is configured to determine the location of the respirator using at least one of a GPS coordinate and a user entry.

21. The respirator system according to claim 6, wherein the flow rate is used to determine a total volume of air breathed.

22. A method of determining a state of a respirator that includes a filter and a motor, the method comprising:

calculating a flow rate through the respirator using steady state motor power and a predetermined characterization of the respirator;

transmitting data corresponding to the flow rate and a pressure in the respirator;

receiving the data with an electronic device; and determining a state of the respirator using the data and the electronic device.

23. The method according to claim 22, wherein the steady state motor power is raw motor power minus acceleration motor power.

* * * * *